(12) United States Patent
Ikebukuro et al.

(10) Patent No.: US 8,367,329 B2
(45) Date of Patent: Feb. 5, 2013

(54) METHOD OF DETECTING INTERACTION BETWEEN NUCLEIC ACID AND PROTEIN, AND APPARATUS FOR THE SAME

(75) Inventors: Kazunori Ikebukuro, Fuchu (JP); Ryo Katayama, Kobe (JP); Eiji Takahashi, Kobe (JP); Hiroyuki Takamatsu, Kobe (JP)

(73) Assignees: National University Corporation Tokyo University of Agriculture and Technology, Tokyo (JP); Kobe Steel, Ltd., Hyogo (JP)

( * ) Notice: Subject to any disclaimer, the term of this patent is extended or adjusted under 35 U.S.C. 154(b) by 1028 days.

(21) Appl. No.: 12/308,370

(22) PCT Filed: Jun. 14, 2007

(86) PCT No.: PCT/JP2007/062053
§ 371 (c)(1),
(2), (4) Date: Dec. 12, 2008

(87) PCT Pub. No.: WO2007/145298
PCT Pub. Date: Dec. 21, 2007

(65) Prior Publication Data
US 2010/0159451 A1 Jun. 24, 2010

(30) Foreign Application Priority Data
Jun. 16, 2006 (JP) .................................. 2006-167898

(51) Int. Cl.
C12Q 1/68 (2006.01)
(52) U.S. Cl. ......................................................... 435/6.1
(58) Field of Classification Search .................. None
See application file for complete search history.

(56) References Cited

U.S. PATENT DOCUMENTS

| 4,243,327 | A | * | 1/1981 | Frosch et al. | ................. 356/432 |
| 6,884,582 | B1 | * | 4/2005 | Chaton et al. | ................. 435/6.16 |
| 2004/0203049 | A1 | * | 10/2004 | Schembri | ......................... 435/6 |

FOREIGN PATENT DOCUMENTS

| EP | 0 594 412 A1 | 10/1993 |
| FR | 2 799 281 | 9/1999 |
| JP | 2003-510600 | 9/2000 |
| JP | 2004-016132 | 6/2002 |
| JP | 2005-110529 | 10/2003 |
| WO | WO 01/06243 A1 | 1/2001 |
| WO | WO 02/90912 A1 | 11/2002 |
| WO | WO 2004/025278 A1 | 3/2004 |
| WO | WO 2005/113817 A2 | 5/2005 |
| WO | WO 2005/113817 A3 | 5/2005 |

OTHER PUBLICATIONS

Extemded European Search Report for PCT/JP2007/062053 mailed Sep. 30, 2009.
Hajime Sakashita et al., "Homogeneous Immunoassay Using Photothermal Beam Deflection Spectroscopy", Analytical Chemistry, vol. 67, No. 7, Apr. 1, 1995, pp. 1278-1282.
Jianhua Zhao et al., "Thermophysical Property Measurements Using Time-Resolved Photothermal Deflection Spectrometry with Step Optical Excitation", Applied Physics letters, vol. 84, No. 26, Jun. 28, 2004, pp. 5332-5334.
Tamao Odake et al., "High-Speed Separation Using Miniaturized Slab Gel and High Spatial Resolution Detection by Thermal Lens Microscope", Part of the EUROPTO Conference on Laser-Tissue Interaction and Tissue Optics V, Sep. 1996, SPIE vol. 3565, pp. 126-133.
K.Adelhelm et al., "Development of a Sensitive Detection System Based on the Photothermal Effect for Biomolecular Interaction Studies", SPIE vol. 2629 (1993), pp. 325-333.
International Search Report for PCT/JP2007/062053 mailed Aug. 28, 2007.
Ryo Mawatari et al., A New Absorptiometric Analyzing Technology by Laser Interferometric Photo-Termal Method for Bioscience, in Japanese (listed on Search Report above), 2005.
Summons to attend Oral Proceedings, from the European Patent Office, in corresponding European Patent Application No. 07745310.8, dated Aug. 9, 2012, pp. 1-5.

* cited by examiner

*Primary Examiner* — Ann Lam
(74) *Attorney, Agent, or Firm* — Stites & Harbison, PLLC; Juan Carlos A. Marquez, Esq; Stephen J. Wever, Esq (57) ABSTRACT

The invention is to easily detect an interaction between nucleic acid and protein with high sensitivity without the need of sample labeling with a fluorescent molecule or sample anchorage onto a metal thin-film. As means for it, the presence or absence of occurrence of the interaction between nucleic acid and protein in a sample (S) is detected in an optical manner. Specifically, the sample (S) is irradiated with excitation rays (Le) and with measuring rays (L2) for measuring a photothermal effect produced in the sample (S) through the irradiation with the excitation rays (Le). A measurement signal for the photothermal effect in the sample (S) by the excitation rays (Le) is produced on the basis of any phase change of the measuring rays (L2). A temporal variation in the measurement signal is used for making a judgment on the presence or absence of any occurrence of interaction between nucleic acid and protein.

9 Claims, 7 Drawing Sheets

METHOD OF DETECTING INTERACTION BETWEEN NUCLEIC ACID AND PROTEIN, AND APPARATUS FOR THE SAME

TECHNICAL FIELD

The present invention relates to an art of detecting interaction between nucleic acid and ligand protein thereof in a sample, for the purpose of detection of a cancerous marker protein, search for a transcription factor, or the like.

BACKGROUND ART

As the method of detecting interaction between nucleic acid and protein, there is conventionally known a so-called fluorescent method given in Patent Document 1 described below. This method includes labeling both a nucleic acid and a protein with fluorescent stain different from each other and measuring on whether the fluorescent stain act mutually to change the fluorescence to detect an interaction between the nucleic acid and the protein.

The fluorescent method requires a pretreatment process having several stages for specifically staining the nucleic acid and the protein with the fluorescent molecules, thus taking a great deal of time and labor before an actual measurement process. Besides, the fluorescent molecules may affect an active region.

As the method of detecting interaction between molecules without the need of labeling with the fluorescent molecules or the like, an SPR (surface-localized plasmon resonance) sensor can be employed. This method includes bonding a sample in a solid phase onto a metal thin-film formed on a substrate and detecting an absorption degree of the sample, using the SPR sensor, when a predetermined laser beam is incident on the sample.

However, this method is practically hard to be utilized for detecting nucleic acid-protein interaction. The method requires control of the thickness of the metal thin-film in the order of nanometer, and further requires absorption of a molecule for capturing a target molecule called "analyte" (e.g., an antibody to an antigen) into the surface of the thin-film, which makes it extremely hard to create a highly-reproducible substrate. Particularly in measuring a functional molecule, an active region needs to be placed near the surface of a substrate, thus possibly being subjected to influence of the substrate.

Patent Document 1: Japanese Patent Laid-Open Publication No. 2004-16132

DISCLOSURE OF THE INVENTION

It is an object of the present invention to provide a method and an apparatus for detecting interaction between nucleic acid and protein easily with high sensitivity without the need of sample labeling with a fluorescent molecule or sample fixing onto a metal thin-film. In order to accomplish the object, the inventors paid attention to a photothermal effect given by the sample containing nucleic acid and protein, that is, the fact that the sample receives and absorbs predetermined excitation rays to generate heat, and thus have found out a conspicuous correlation between the photothermal effect and the presence or absence of the interaction between nucleic acid and protein in the sample. Specifically, although generally decreasing as time elapses, the photothermal effect is little reduced with time, in a sample with an interaction between nucleic acid and protein, at least immediately after the photothermal effect begins to rise. This is probably because the interaction between the nucleic acid and the ligand protein stabilizes the fragment structure of the nucleic acid.

The present invention is provided for detecting interaction between nucleic acid and protein in a sample on the basis of the above correlation. Specifically, a detection method according to the present invention includes the steps of: irradiating the sample with excitation rays; measuring a photothermal effect produced in the sample through the irradiation with the excitation rays; and making a judgment on the presence or absence of interaction between nucleic acid and protein, on the basis of a temporal variation in the photothermal effect. In addition, a detection apparatus according to the present invention includes: a sample storage portion storing the sample; an excitation-light irradiation system irradiating the sample stored in the sample storage portion with excitation rays; and a measuring device producing a measurement signal for a photothermal effect produced in the sample through the irradiation with the excitation rays, the measuring device including a signal processor creating data on a temporal variation in the measurement signal to make a judgment on the presence or absence of the interaction, on the basis of the data.

The above detection method and the detection apparatus are capable of detecting nucleic acid-protein interaction in the sample easily with high sensitivity on the basis of a temporal variation in a photothermal effect only by irradiating a sample with excitation rays and measuring the photothermal effect in the sample.

BEST MODE FOR IMPLEMENTING THE INVENTION

A first embodiment of the present invention will be described with reference to FIGS. 1 to 5.

Figure 1:
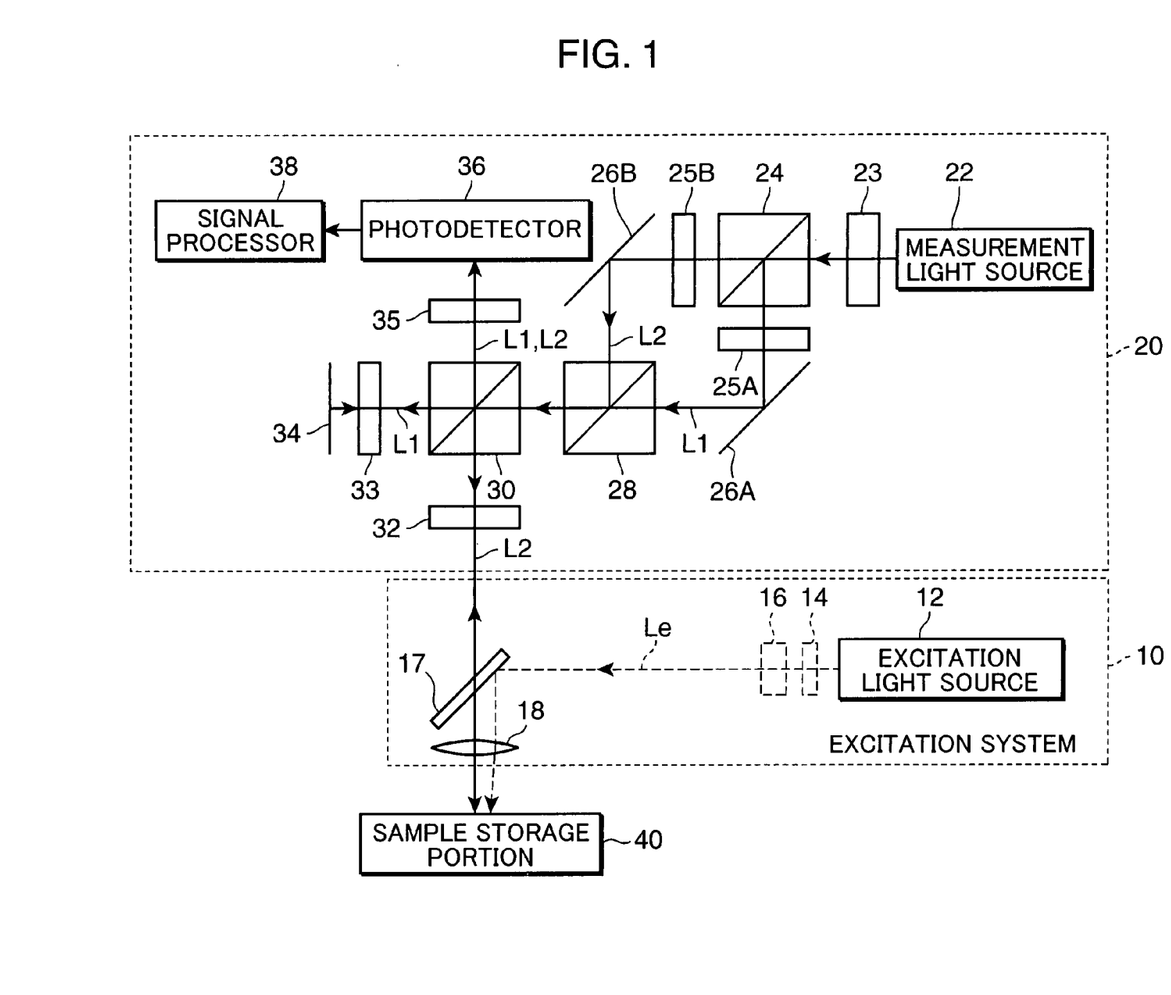
FIG. 1 is a block diagram showing an entire configuration of a detection apparatus for detecting interaction between nucleic acid and protein according to a first embodiment of the present invention.

FIG. 1 is showing an entire configuration of a detection apparatus according to this embodiment. The detection apparatus includes an excitation light irradiation system (below called simply the "excitation system") 10, a measurement system (measuring device) 20, and a sample storage portion 40 storing a sample (described later).

The excitation system 10, for irradiating the sample stored at a predetermined position in the sample storage portion 40 with excitation rays, includes an excitation light source 12, a spectroscopic system 14, a modulation system 16, a dichroic mirror 17 and a condensing lens 18.

The excitation light source 12 may preferably be, for example, a xenon lamp outputting white light or a mercury lamp outputting ultraviolet light. The rays emitted from the excitation light source 12 are dispersed by the spectroscopic system 14 and cyclically modulated by the modulation system 16, thereby becoming excitation rays Le suitable for measurement.

The dichroic mirror 17, located between the measurement system 20 and the sample storage portion 40, allows measuring rays coming from the measurement system 20 as described later to directly pass through, while reflecting the excitation rays Le coming from the excitation light source 12 in the direction perpendicular thereto, thus leading the excitation rays Le, coaxially with the measuring rays, to the sample storage portion 40. The condensing lens 18 condenses the excitation rays Le reflected by the dichroic mirror 17 into a specified area to irradiate the sample stored in the sample storage portion 40 with the excitation rays Le. The sample absorbs the excitation rays Le to generate heat, thereby causing a variation in the temperature thereof to change the refractive index of the sample.

The measurement system 20 is to irradiate the sample with measuring rays L2 for measuring a refractive index of the sample and measure the refractive index based on a phase change in the measuring rays. The measurement system 20 according to this embodiment includes a measurement light source 22, an essential optical system, a photodetector 36 and a signal processor 38. The optical system includes a plurality of polarization beam splitters 24, 28 and 30, a plurality of acousto-optic modulators 25A and 25B, a plurality of mirrors 26A, 26B and 34, a plurality of quarter-wave plates 23, 32 and 33, and a polarizing plate 35.

The measurement light source 22 comprises, for example, a 1 mW-power He—Ne laser. The λ/2-wave plate 23 of the optical system adjusts the polarization plane of light applied from the measurement light source 22. The polarization beam splitter 24 splits the light subjected to the polarization-plane adjustment into two polarized rays perpendicular to each other; reference rays L1 and the measuring rays L2.

The reference rays L1 enter the acousto-optic modulator 25A, which shifts (converts) the frequency of the reference rays L1. The reference rays L1 reflect off the mirror 26A to enter the polarization beam splitter 28. On the other hand, the measuring rays L2 enter the acousto-optic modulator 25B, which shifts (converts) the frequency of the measuring rays L2. The measuring rays L2 reflect off the mirror 26B to enter the polarization beam splitter 28, in which the measuring rays L2 and the reference rays L1 are synthesized.

The reference rays L1 directly pass through the polarization beam splitter 30 and reflect off the mirror 34 to return straight to the polarization beam splitter 30. The quarter-wave plate 33, arranged between the polarization beam splitter 30 and the mirror 34, allows the reference rays L1 to go and come back through the quarter-wave plate 33, thereby turning the polarization plane of the reference rays L1 by 90°. Accordingly, the reference rays L1 which has returned to the polarization beam splitter 30 are reflected by 90° toward the opposite side to the sample storage portion 40, thereby entering the photodetector 36 through the polarizing plate 35.

The measuring rays L2 are reflected by 90° toward the sample storage portion 40 by the polarization beam splitter 30 to be led to the sample storage portion 40 through the quarter-wave plate 32, the dichroic mirror 17 of the excitation system 10 and the condensing lens 18. the measuring rays L2 are incident upon a sample as described later, and further reflected by 180° to return through the quarter-wave plate 32 to the polarization beam splitter 30. At this time, the measuring rays L2 go and come back through the quarter-wave plate 32, thereby turning the polarization plane of the measuring rays L2 by 90°. Accordingly, the measuring rays L2 directly pass through the polarization beam splitter 30 to merge with the reference rays L1 and go to the polarizing plate 35 and the photodetector 36. The polarizing plate 35 allows an interference between the reference rays L1 and the measuring rays L2, and the photodetector 36 converts the intensity of a interference light generated by the interference into an electric signal (measurement signal).

The signal processor 38 samples the measurement signal at specified sampling cycles and calculates a phase change of the measuring rays L2 (measuring rays) on the basis of the measurement signal. Besides, the signal processor 38 creates data on a temporal variation in the phase change, and, as described later, automatically makes a judgment on the presence or absence of the interaction in a sample S on the basis of the above data.

Herein, the interference light intensity S1 is given in the following expression (1).

$$S1 = C1 + C2 \cdot \cos(2\pi \cdot fb \cdot t + \phi) \qquad (1)$$

In this expression, C1 and C2 are constants determined according to the optical system such as a polarization beam splitter or the transmittance of the sample S; φ is a phase difference made by the optical-path length difference between the reference rays L1 and the measuring rays L2; and fb is the difference in frequency between the reference rays L1 and the measuring rays L2. The expression (1) indicates that the change of the phase difference φ is obtained from a variation in the interference light intensity S1 (the difference between the intensity of interference light when the excitation rays are not applied or the intensity thereof is weak and the intensity of interference light when the intensity of the excitation rays is great). The signal processor 38 calculates the change in the phase difference φ according to the expression (1).

If the intensity of the excitation rays Le is cyclically modulated at a frequency f by the rotation of a chopper for example, then the refractive index of the sample S also varies according to the frequency f, the optical-path length of the measuring rays L2 varies according to the frequency f as well (the optical-path length of the reference rays L1 is unchanged), and further, the phase difference φ varies according to the frequency f. Accordingly, the measurement (calculation) of the change of the phase difference φ for a component of the frequency f (a component of the cycle equal to an intensity modulation cycle of the excitation signal), enables measurement of only a variation in the refractive index of the sample S without the effect of a noise containing no component of the frequency f. This measurement improves an S/N ratio in measuring the phase difference φ.

When the excitation light source 12 is a laser diode, an LED or the like, control of the power supply of the excitation light source 12 by an electric circuit also enables the above modulation.

Figure 2:
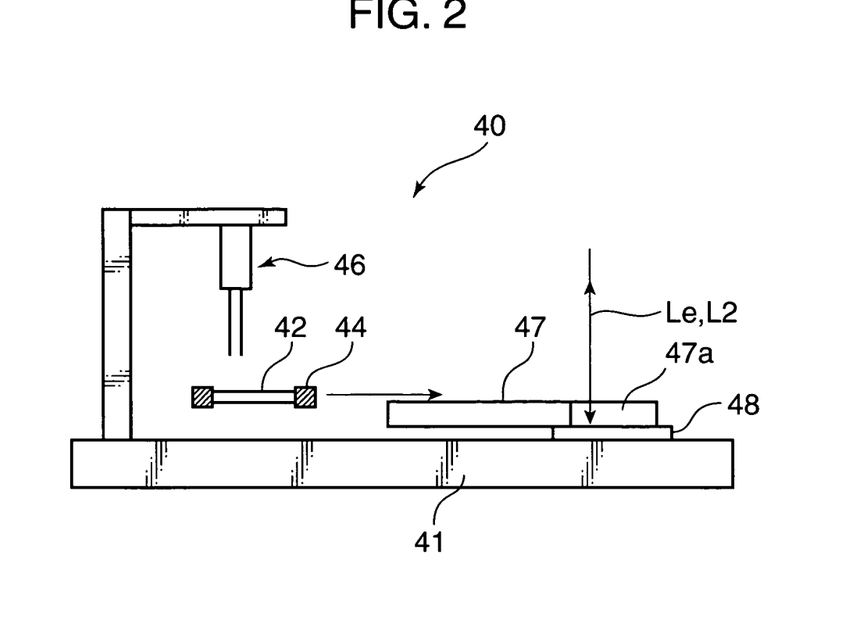
FIG. 2 is a partly-sectional front view of a sample storage portion in the detection apparatus.

The sample storage portion 40 includes, as shown in FIG. 2, a base 41, a micro-array 42 as a sample container and a manipulator 44 as a transfer means, the base 41 being provided thereon with an automatic distribution injector 46, a heater 47 and a mirror 48.

Figure 3:
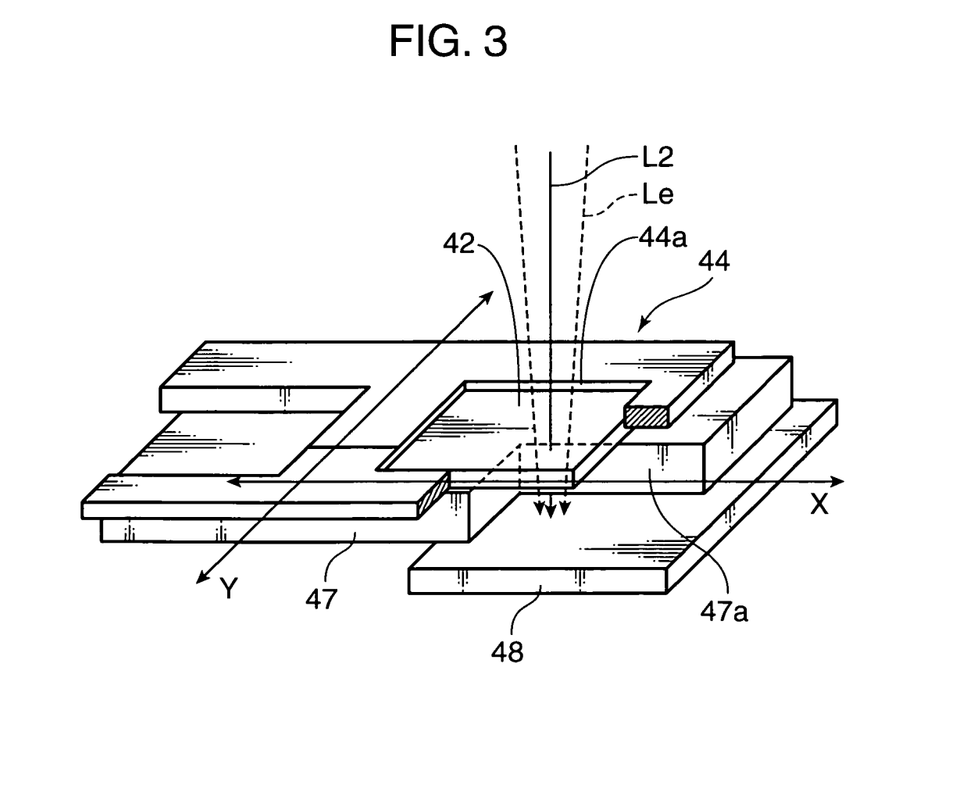
FIG. 3 is a partly-sectional perspective view of a main part of the sample storage portion.
Figure 4A:
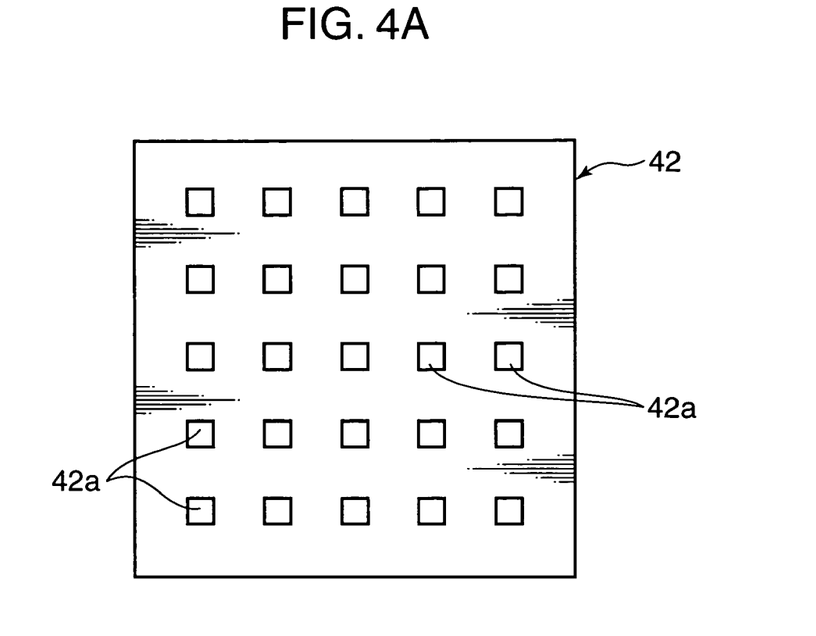
FIG. 4A is a plan view of a micro-array used in the sample storage portion.
Figure 4B:
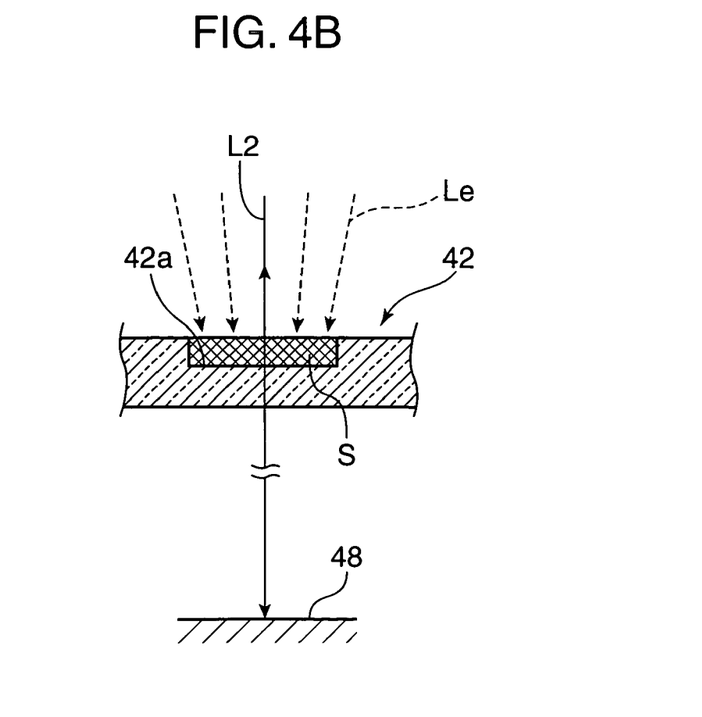
FIG. 4B is a sectional view of a main part thereof.

The micro-array 42, for storage of the sample separately poured from the automatic distribution injector 46, consists of a flat substrate shown in FIGS. 2 to 4. The micro-array 42 has an upper surface portion in which a plurality of (5×5=25 in the example of FIG. 4A) sample storage concaves 42a are formed and arranged lengthwise and crosswise, to allow the sample S shown in FIG. 4B to separately injected into each of the sample storage concaves 42a. Although the present invention does not limit the material of the sample container to a specific one, the material of the micro-array 42 according to this embodiment is required to allow the excitation rays Le and the measuring rays L2 to pass through; for example, synthetic quartz, quartz or PDMS is preferably used.

The manipulator 44 includes a window 44a having a shape corresponding to the outline of the micro-array 42, and holds the micro-array 42 fitted into the window 44a. In other words, the manipulator 44 holds the micro-array 42 from every outside direction while opening the micro-array 42 up and down.

The automatic distribution injector 46, standing on the base 41, drops the sample S in a proper quantity (i.e., a quantity for filling each sample storage concave 42a).

The mirror 48, arranged horizontally apart from the automatic distribution injector 46 on the base 41, reflects the measuring rays L2 introduced downward from the measurement system 20 upward by 180°.

The heater 47, which corresponds to the temperature regulation system according to the present invention, is provided right over the mirror 48 to heat the micro-array 42 transferred thereto to a predetermined temperature for accelerating the interaction between nucleic acid and protein in the sample S (reaction temperature). The heater 47 is formed with a notch 47a in a position into which the excitation rays Le and the measuring rays L2 are applied, the notch 47a opening the mirror 48 above. The temperature regulation system according to the present invention is not limited to the heater 47 but may include a cooler for lowering the temperature of a sample to the contrary.

The manipulator 44 transfers the micro-array 42 to a distribution-injection position for the injection from the automatic distribution injector 46, a heating position over the heater 47 and an irradiation position for irradiation with the excitation rays Le and the measuring rays L2 on the mirror 48, in this order.

Next, an operation will be described of this detection apparatus.

In the sample storage portion 40, the manipulator 44 holding the micro-array 42 transfers the micro-array 42 to the distribution-injection position. In detail, it moves the micro-array 42 so as to let each sample storage concave 42a of the micro-array 42 to be set one by one to a corresponding distribution-injection position thereof right under the automatic distribution injector 46. At the distribution-injection position, the automatic distribution injector 46 injects the sample S separately into each sample storage concave 42a.

After the separate injections of the sample S into all of the sample storage concaves 42a, the manipulator 44 transfers the micro-array 42 to the heating position over the heater 47. The heating position may be a position where the micro-array 42 is in direct contact with the heater 47 or a position where it is slightly apart from the heater 47. The manipulator 44 holds the micro-array 42 for a predetermined time at the heating position to thereby accelerate the reaction (interaction between nucleic acid and protein) in the sample S inside of each sample storage concave 42a.

Thereafter, the manipulator 44 transfers the micro-array 42 to the irradiation position for the irradiation with the excitation rays Le and the measuring rays L2 shown in FIG. 4B (the position corresponding to the notch 47a of the heater 47 and right over the mirror 48). Then, it moves the micro-array 42 so as to irradiate the sample S inside of each sample storage concave 42a of the micro-array 42 one after another with the excitation rays Le and the measuring rays L2.

At the irradiation position, the excitation rays Le led to the sample storage portion 40 from the excitation system 10 are incident upon the sample S and pass through it. At this time, the sample S absorbs the excitation rays to thereby generate heat (a photothermal effect). Meanwhile, the measuring rays L2 introduced to the sample storage portion 40 from the measurement system 20 are incident upon each sample storage concave 42a coaxially with the excitation rays and pass through the sample S inside of the concaves 42a. Sequentially, the measuring rays L2 are reflected upward by the mirror 48 and further pass through the sample S. At this time, since the refractive index in the sample S varies with the quantity of heat generated through the photothermal effect and the phase difference $\phi$ varies with the refractive index, the intensity of the interference light generated by the interference between the measuring rays L2 returned to the measurement system 20 and the reference rays L1 in the measurement system 20 varies with the generated-heat quantity. The photodetector 36 of the measurement system 20 creates a measurement signal corresponding to the interference light intensity and input it into the signal processor 38.

Figure 5:
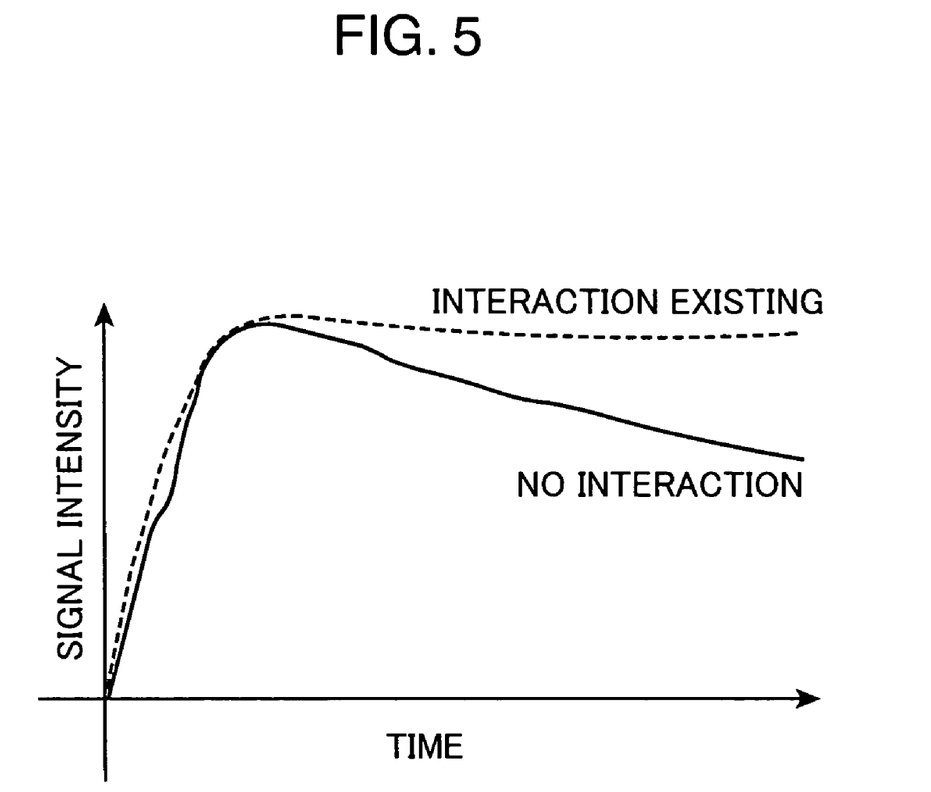
FIG. 5 is a graphical representation showing a temporal variation in the intensity of a measurement signal generated by the detection apparatus.

The signal processor 38 acquires the measurement signal at predetermined sampling cycles to create a data indicating a temporal variation in the measurement signal, for example, a graph, as shown in FIG. 5, showing the relationship between elapsed time and signal intensity. No occurrence of interaction between nucleic acid and protein in the sample S allows the signal intensity to lower as time elapses, while any occurrence of the interaction keeps the signal intensity substantially at a constant value over time. In order to utilize this characteristic, the signal processor 38 calculates a temporal attenuation rate of the signal intensity, and judges that any interaction exists when the temporal attenuation factor is a specified value or below.

Although the temporal attenuation rate may be recognized from the graph by a person, the signal processor 38 in this embodiment automatically calculates the temporal attenuation rate and makes a judgment on the presence or absence of the interaction. For example, on the basis of a signal intensity acquired at each sampling cycle, the signal processor 38 can calculate a linear approximate expression indicating a temporal variation in the signal intensity, and make a judgment that the interaction has occurred, based on the gradient of the line equal to or smaller than a specified value. Besides, a measurement may be assumed to be faulty based on a excessive variation of the sample signals from the linear approximate expression.

The above-mentioned detection method and detection apparatus are capable of detecting interaction between nucleic acid and protein in the sample S without labeling the nucleic acid and the protein in the sample S or anchoring the sample S onto a metal thin-film.

Next, a second embodiment of the present invention will be described with reference to FIGS. 6 and 7. The configuration of the whole apparatus is the same as that of FIG. 1 and the disclosure thereof is omitted here.

Figure 6A:
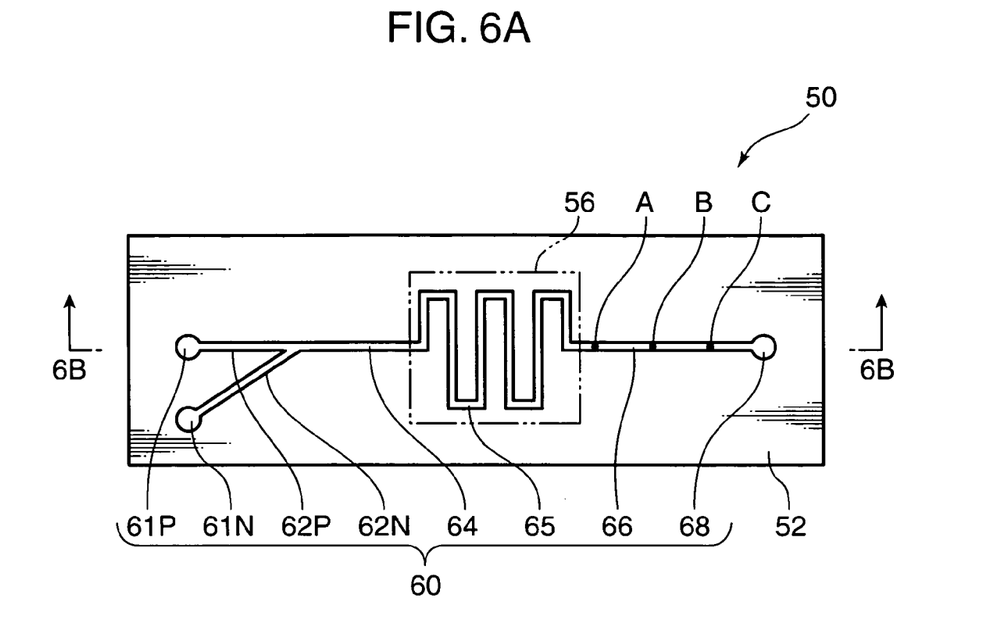
FIG. 6A is a plan view of a micro-reactor used in a second embodiment of the present invention.
Figure 6B:
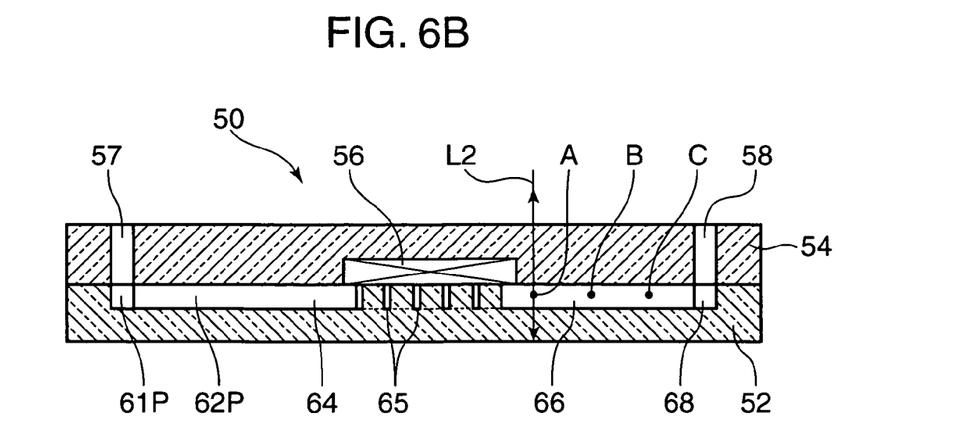
FIG. 6B is a sectional view along a 6B-6B line of FIG. 6A.
Figure 7A:
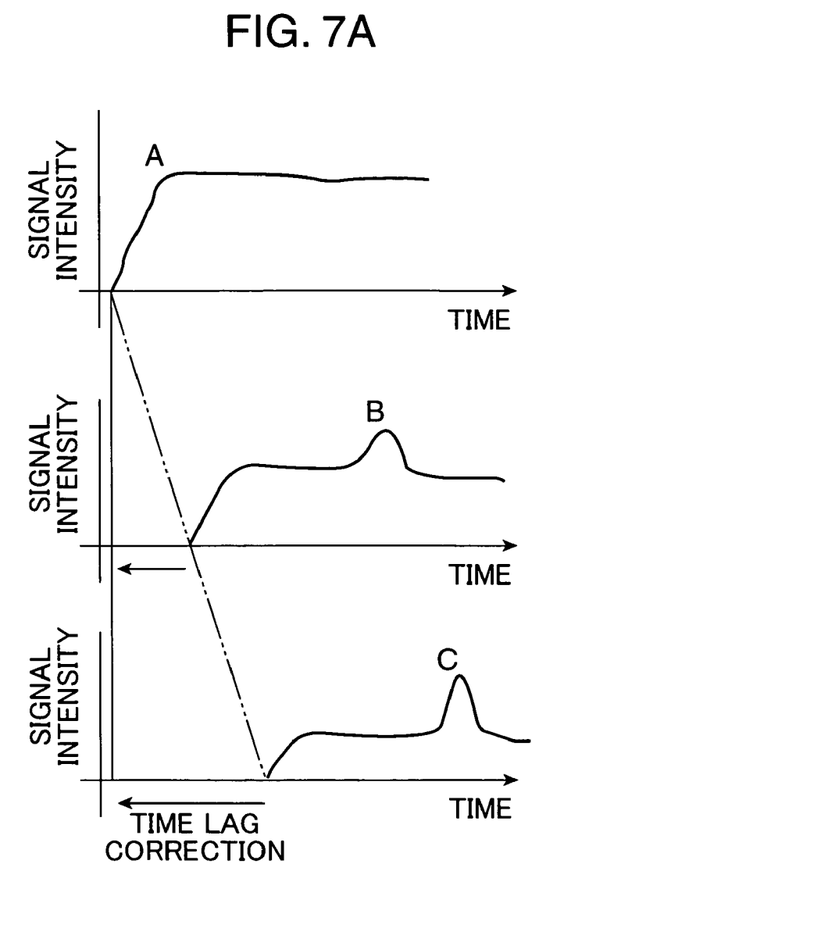
FIG. 7A is a graphical representation showing a temporal variation in a measurement signal at each measurement position A to C obtained in the second embodiment.

In the second embodiment, the means for transferring the micro-array 42 itself as a sample container according to the first embodiment is replaced with a micro-reactor 50 including a flow path 60 for letting a sample flow in a specified direction as shown in FIG. 6. In other words, the micro-reactor 50 functions as both a sample container and a means for guiding a sample in a transfer direction.

The micro-reactor 50 includes a lower substrate 52 and an upper substrate 54 placed thereon. These substrates 52 and 54 are both made of a material allowing the excitation rays Le and the measuring rays L2 to pass through in the same way as the above-mentioned micro-array 42.

The flow path 60 is a groove formed in the upper surface of the lower substrate 52. The upper substrate 54 is placed and joined onto the lower substrate 52 to thereby seal the flow path 60.

The flow path 60 includes, in order from upstream: a nucleic-acid supply portion 61N and a protein supply portion 61P; supply passages 62N and 62P downstream from each supply portion 61N, 61P, respectively; a merging passage 64 into which the supply passages 62N and 62P; a reaction portion 65 for conducting a reaction of the merged and mixed nucleic acid and protein; a light irradiation portion 66 to which the excitation rays Le and the measuring rays L2 are applied in the substrate-thickness direction; and a sample discharge portion 68.

The nucleic-acid supply portion 61N and the protein supply portion 61P are supplied with nucleic acid and protein composing a sample, respectively. Each supply portion 61N, 61P leads to a supply hole 57 penetrating the upper substrate 54 in the thickness direction, and similarly, the sample discharge portion 68 leads to a discharge hole 58 formed in the upper substrate 54. To the supply holes 57 are connected a nucleic-acid supply syringe and a protein supply syringe as a sample transferring means respectively. The syringes supply nucleic acid and protein through the supply hole 57 to the nucleic-acid supply portion 61N and the protein supply portion 61P, respectively.

There is embedded a heater 56 into the upper substrate 54, so as to be positioned over the reaction portion 65. The heater 56 heats the mixture sample of nucleic acid and protein to a reaction temperature thereof. In order to lengthen this heating time or reaction time sufficiently (e.g., 10 minutes), the reaction portion 65 zigzags to thereby make the passage longer.

The light irradiation portion 66 runs straight and has a plurality of irradiation positions (three positions A, B and C in the figure) to which the excitation rays Le and the measuring rays L2 are applied respectively, the irradiation positions arranged in the longitudinal direction (i.e., the sample-flow direction) of the light irradiation portion 66. The irradiation positions or the micro-reactor 50 is shifted so as to let the rays Le and L2 be applied to the irradiation positions one by one.

The bottom surface of the lower substrate 52 is coated with a reflection film (e.g., dielectric multi-layer film) for reflecting the measuring rays L2 by 180°. This reflection film lets the measuring rays L2 go and come back through the sample S by the reflection of the measuring rays L2.

The dimensions of the flow path 60 can be suitably set, and preferably, it may generally have a width of approximately 200 μm and a depth of approximately 100 μm. The sample is preferably conveyed at a relatively low speed, which is preferably about 0.5 mm/sec for example.

In the micro-reactor 50, all of the above supply, the mixing, the reaction and the photothermal-effect measurement of nucleic acid and protein can be preformed. This enables efficient detection of nucleic acid-protein interaction in a compact configuration.

The signal processing according to the second embodiment is executed, for example, in the following way.

If there is no occurrence of interaction between nucleic acid and protein in the sample, the photothermal effect by irradiation with the excitation rays Le attenuates as time passes, thereby lowering the intensity of a detection signal at the downstream position B than that at the position A as a measurement start position and lowering the intensity of a detection signal at the further downstream position C than that at the position B. On contrast, if any interaction occurs at a part in the sample, the photothermal effect hardly attenuates at that part, thereby heightening the signal intensity temporarily when the part passes the position B and the position C. This temporal variation in the signal intensity is as shown, for example, in FIG. 7A. Since time lags exist among the detection signals at the positions A to C, the detection signals in the positions A to C should be corrected. When the corrected signals superposed to each other as shown in FIG. 7B, the intensity of the superposed signal heightens significantly only at the interaction occurrence part (D in the same figure). This makes it possible to grasp the fact that there is interaction at such locally-higher signal-intensity part.

Figure 7B:
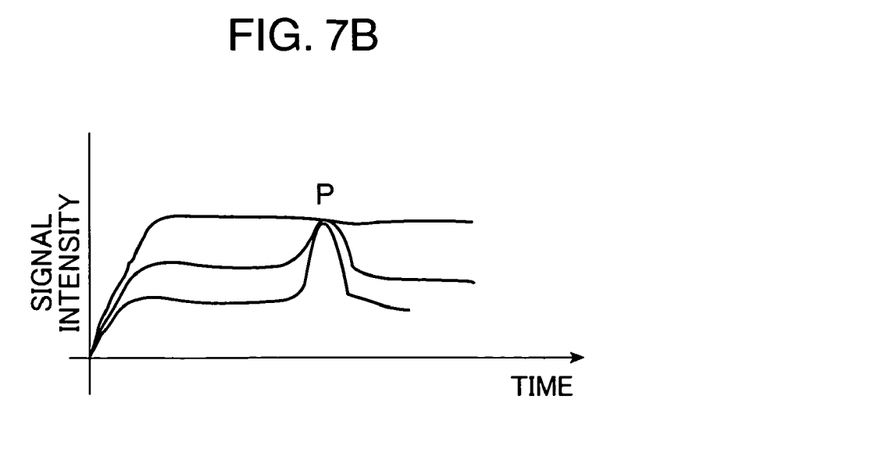
FIG. 7B is a graphical representation showing a temporal variation in each measurement signal superposed on one another.

The signal processor 38 outputs the superposed data shown in FIG. 7B, and further automatically makes a judgment, according to the level of a peak value in the superposed data, whether there is any interaction. In the second embodiment, similarly to the first embodiment, the irradiation position for the excitation rays Le and the measuring rays L2 may be set to a single position and a temporal variation therein can be monitored. Alternatively, the irradiation position for the excitation rays Le and the measuring rays L2 may be tracked at a speed equivalent to the sample flow speed in the light irradiation portion 66.

The method of measuring a sample photothermal effect with the excitation rays according to the present invention is not limited to the above optical interference method. For example, a method of measuring a variation in the intensity of measuring rays according to the refractive index of a solvent changes, like a thermal lens method, can also be used.

PRACTICAL EXAMPLE

There is performed a detection of nucleic acid-protein interaction in the apparatus shown in FIGS. 1 to 4. The micro-array 42 shown in FIGS. 4A and 4B is made of synthetic quartz, and each sample storage concave 42a is shaped like a rectangular parallelepiped of 0.5 mm×0.5 mm×1.0 mm (alternatively, it may be, for example, a cylindrical column having a diameter of 0.5 mm). A sample composed of a solution obtained by mixing protein thrombin and aphthamer (a functional polymer containing DNA or RNA) as a nucleic acid capable of making a specific reaction to the thrombin is injected into each sample storage concave 42a. The mixing ratio is a ratio for making the end concentration of the thrombin 70 nM and the end concentration of the aphthamer 175 nM.

After the injection, the sample is heated to 37° C. by the heater 47 and kept 15 minutes as it is. Thereafter, the sample is set to the irradiation position for the excitation rays Le and the measuring rays L2, and a photothermal effect in the sample is measured. A high-pressure mercury lamp is employed as the light source 12 of the excitation rays Le, and a luminous maximum area near a wavelength of 250 nm thereof is extracted through a band pass filter and modulated to approximately 80 Hz by an optical chopper. The excitation rays Le are concentrated upon an area having a diameter of 5 mm to be applied to the sample. Further, the measuring rays L2 are applied to the sample coaxially with the excitation rays Le, and the intensity of interference light of the measuring rays L2 and the reference rays L1 is measured. This measurement signal is displayed as a voltage value in the signal processor 38 and then continuously recorded by a data logger.

Figure 8:
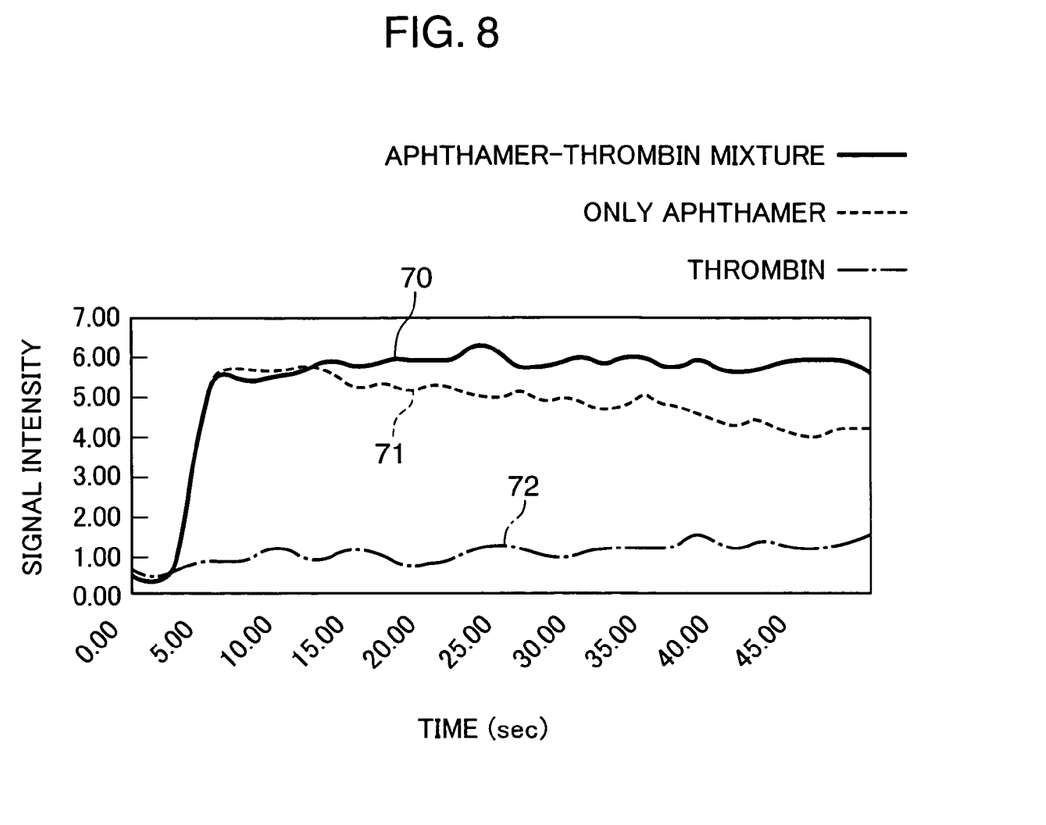
FIG. 8 is a graphical representation showing measurement signals obtained by implementing the apparatus according to the first embodiment.

FIG. 8 shows the result of the measurement. As given by a broken line 71 in the figure, if the sample contains only the aphthamer, the intensity of the measurement signal rises and then falls gradually. On the other hand, as given by a single-dot chain line 72 in the figure, if the sample contains only the thrombin, the signal intensity does not rise. In contrast, if the sample is a mixture of the aphthamer and the thrombin, as given by a solid line 70 in the figure, the signal intensity rises and is kept almost without any fall. This result means that comparison of the falling speed of the measurement signal after it has risen enables an judgment on the presence or absence of the interaction between aphthamer and thrombin. Specifically, it is verified that the existence of thrombin mixed with aphthamer can be detected on the order of approximately 40 nM.

As described so far, the present invention provides a method and an apparatus capable of detecting interaction between nucleic acid and protein in a sample. The method includes the steps of: irradiating the sample with excitation rays; measuring a photothermal effect produced in the sample through the irradiation with the excitation rays; and making a judgment on the presence or absence of the interaction between nucleic acid and protein, on the basis of a temporal variation in the photothermal effect. In addition, the apparatus includes: a sample storage portion storing the sample; an excitation light irradiation system irradiating the sample stored in the sample storage portion with excitation rays; and a measuring device producing a measurement signal of a photothermal effect produced in the sample through the irradiation with the excitation rays, the measuring device including a signal processor creating data on a temporal variation in the measurement signal and making a judgment on the presence or absence of the interaction on the basis of the data.

In the detection method and the detection apparatus, the measurement of a photothermal effect by irradiating the sample with excitation rays and the monitoring of a temporal variation in the measured photothermal effect enable an accurate judgment on the presence or absence of the interaction between nucleic acid and protein in the sample. Thereby, interaction between nucleic acid and protein in the sample can be easily detected with high sensitivity without labeling the nucleic acid and the protein in the sample or anchoring the sample onto a metal thin-film. Besides, in the detection apparatus, the signal processor creates data useful for a judgment on the presence or absence of the interaction and automatically makes the judgment on the basis of the data.

The detection method is suitable, for example, for detection of the presence or absence of the interaction between a functional polymer (so-called aphthamer) containing DNA or RNA and ligand protein thereof.

In the detection method, the step of measuring the photothermal effect may preferably include making measuring rays other than the excitation rays pass through the sample and measuring a phase change of the measuring rays by the pass. Similarly, in the detection apparatus, the measuring device may preferably make measuring rays other than the excitation rays pass through the sample and measure a phase change of the transmitted measuring rays by the pass. Since the heat generation in the sample through a photothermal effect changes the refractive index of light, making the measuring rays pass through the sample and measuring the phase change thereof enable the photothermal effect of the sample to be grasped easily and accurately.

In this case, it is more desirable that the measuring device includes: a measurement light source; an optical system making measuring rays emitted from the measurement light source pass through the sample stored in the sample storage portion and interfere with reference rays; and a photodetector detecting an intensity of the rays produced by the interference. This measuring device can easily measure a phase change of the measuring rays passing through the sample, using a simple configuration which is required only to make the measuring rays interfere with reference rays and to detect an intensity of the interference rays produced by the interference.

The sample storage portion may preferably include: a sample container storing the sample; a temperature regulation system regulating the temperature of the sample in the sample container to a temperature for a reaction of the nucleic acid and the protein; and a transferring means for transferring the heated sample to an irradiation position for irradiation with the excitation rays. In this sample storage portion, a reaction (interaction) of the nucleic acid and the protein inside of the sample can be conducted in the sample container, where the sample can be directly irradiated with the excitation rays, following the reaction therein.

It is preferable that the transferring means transfers the sample container to an injection position for injecting the sample into the sample container, a temperature regulation position for regulating the temperature of the injected sample using the temperature regulation system and an irradiation position for the irradiation with the excitation rays, in this order.

The sample storage portion may include a flow path along which the sample flows, the flow path having, in order from upstream, an introduction portion for introducing each of the nucleic acid and the protein, a mixing portion for merging and mixing the introduced nucleic acid and protein, a reaction portion conducting the reaction by regulating the temperature of the mixture using the temperature regulation system, and an excitation light irradiation portion to which the excitation rays are applied. This sample storage portion enables the transference of the sample within the sample storage portion.

Furthermore, if the excitation light irradiation portion a plurality of positions arranged in the flow direction of the sample for application of the excitation rays, the measurement of the photothermal effect at each of the positions enables a correct detection of the temporal variation in the photothermal effect.

The invention claimed is:

1. A method of detecting the presence or absence of an interaction between nucleic acid and protein in a sample, comprising the steps of:
    irradiating the sample with excitation rays;
    measuring a photothermal effect produced in the sample through the irradiation with the excitation rays to produce a measurement signal; and
    making a judgment on the presence or absence of the occurrence of an interaction between nucleic acid and protein on the basis of a temporal attenuation rate, after the photothermal effect begins to rise, of an intensity of the measurement signal of the photothermal effect.

2. The method of detecting an interaction between nucleic acid and protein according to claim 1, wherein the detection is conducted on the presence or absence of interaction between a functional polymer containing DNA or RNA and ligand protein thereof.

3. The method of detecting an interaction between nucleic acid and protein according to claim 1, wherein the step of measuring the photothermal effect includes making measuring rays other than the excitation rays pass through the sample and measuring a phase change of the measuring rays through the pass.

4. An apparatus for detecting the presence or absence of an interaction between nucleic acid and protein in a sample, comprising:
   a sample storage portion storing the sample;
   an excitation light irradiation system irradiating the sample stored in the sample storage portion with excitation rays; and
   a measuring device producing a measurement signal on a photothermal effect produced in the sample through the irradiation with the excitation rays,
   wherein the measuring device includes a signal processor creating data on a temporal attenuation rate, after the photothermal effect begins to raise, of an intensity of the measurement signal and making a judgment on the presence or absence of the interaction on the basis of the data.

5. The apparatus for detecting an interaction between nucleic acid and protein according to claim 4, wherein the measuring device makes measuring rays other than the excitation rays pass through the sample and measures a phase change of the measuring rays through the pass.

6. The apparatus for detecting an interaction between nucleic acid and protein according to claim 5, wherein the measuring device includes: a measurement light source; an optical system which makes measuring rays emitted from the measurement light source pass through the sample stored in the sample storage portion and interfere with reference rays; and a photodetector detecting an intensity of the rays produced by the interference.

7. The apparatus for detecting an interaction between nucleic acid and protein according to claim 4, wherein the sample storage portion includes: a sample container storing the sample; a temperature regulation system regulating the temperature of the sample in the sample container to a temperature for a reaction of the nucleic acid and the protein; and a transferring means for transferring the heated sample to an irradiation position for irradiation with the excitation rays.

8. The apparatus for detecting an interaction between nucleic acid and protein according to claim 7, wherein the transferring means transfers the sample container to an injection position for injecting the sample into the sample container, a temperature regulation position for regulating the temperature of the injected sample using the temperature regulation system and an irradiation position for irradiating the sample with the excitation rays, in this order.

9. The apparatus for detecting an interaction between nucleic acid and protein according to claim 7, wherein the sample storage portion includes a flow path along which the sample flows, the flow path having, in order from upstream, an introduction portion for introducing each of the nucleic acid and the protein, a mixing portion for merging and mixing the introduced nucleic acid and protein, a reaction portion conducting the reaction by regulating the temperature of the mixture using the temperature regulation system, and an excitation light irradiation portion to which the excitation rays are applied.

* * * * *